United States Patent [19]

James

[11] Patent Number: 4,485,053

[45] Date of Patent: Nov. 27, 1984

[54] PROCESS FOR THE PRODUCTION OF ARYLSULFONYL ISOCYANATES

[75] Inventor: Donald R. James, El Sobrante, Calif.

[73] Assignee: Stauffer Chemical Company, Westport, Conn.

[21] Appl. No.: 486,142

[22] Filed: Apr. 18, 1983

[51] Int. Cl.$^3$ .................. C07C 143/79; C07D 333/00
[52] U.S. Cl. ................................. 260/545 R; 549/65; 549/479
[58] Field of Search .............. 260/545 R; 549/65, 479

[56] References Cited

U.S. PATENT DOCUMENTS 4,379,769  4/1983  Levitt .............................. 260/545 R

FOREIGN PATENT DOCUMENTS 44209   1/1982  European Pat. Off. ........ 260/545 R
64322  11/1982  European Pat. Off. ........ 260/545 R

OTHER PUBLICATIONS

Ulrich et al., "Journal of Organic Chemistry", vol. 34, pp. 3200–3201 (1969).

Primary Examiner—Alan Siegel
Attorney, Agent, or Firm—Joel G. Ackerman

[57] ABSTRACT

Arylsulfonyl isocyanates are prepared by reaction of an arylsulfonylamine with thionyl chloride and chlorocarbonylsulfenyl chloride in the presence of a catalytic amount of a tertiary base. The isocyanates may be used as intermediates in the production of herbicides or pharmaceutically active compounds.

7 Claims, No Drawings

PROCESS FOR THE PRODUCTION OF ARYLSULFONYL ISOCYANATES

BACKGROUND OF THE INVENTION AND PRIOR ART

This invention pertains to a process for the production of arylsulfonyl isocyanates having the formula $ArSO_2NCO$ in which Ar designates phenyl, substituted phenyl, phenoxyphenyl, substituted phenoxyphenyl, thienyl, furyl, naphthyl, or substituted naphthyl.

Compounds of such type have been found useful as intermediates in the synthesis of arylsulfonyl-type herbicidal or plant growth regulant compounds, and hypoglycemic agents.

European Patent Application, Publication No. 44209, of E. I. DuPont de Nemours and Company, discloses production of a number of arylsulfonyl isocyanates as intermediates for herbicides and plant growth regulators, particularly at pages 12–18, 48, 51 and 69. Such methods include reaction of a sulfonamide with phosgene in the presence of an alkyl isocyanate in a solvent such as chlorobenzene, or reaction of a sulfonylurea with phosgene. The addition of a tertiary base to the reaction mixture may be advantageous. One such base mentioned in the European Patent Application, at page 15, is DABCO, or 1,4-diaza[2,2]bicyclooctane. Another method is the reaction of an arylsulfonamide with thionyl chloride to form an intermediate sulfinyl compound which is then reacted with phosgene in the presence of a pyridine catalyst to form the desired arylsulfonyl isocyanate.

European Patent Application Publication No. 64332, of E. I. duPont de Nemours and Company, discloses production of another series of substituted phenylsulfonyl isocyanates as herbicide intermediates, by similar methods. See particularly pp 8–10 and Examples 1, 2 and 6.

SUMMARY OF THE INVENTION

This invention pertains to a process for the production of arylsulfonyl isocyanates having the formula $ArSO_2NCO$ in which Ar represents phenyl, substituted phenyl, phenoxyphenyl, substituted phenoxyphenyl, thienyl, furyl, naphthyl, or substituted naphthyl, comprising reacting, in a single step, an arylsulfonamide having the formula $ArSO_2NH_2$ in which Ar is defined as above, with thionyl chloride and chlorocarbonyl sulfenyl chloride, in the presence of a catalytic amount of pyridine.

The process proceeds according to the reaction $$ArSO_2NH_2 + ClCSCl + SOCl_2 \longrightarrow ArSO_2NCO.$$
(where ClCSCl has a C=O)

DETAILED DESCRIPTION OF THE INVENTION

In general, the process is carried out by mixing the arylsulfonylamide with thionyl chloride, which also serves as a solvent for the reaction. A few drops of pyridine catalyst may be included in this mixture, or optionally added subsequently. An appropriate amount of chlorocarbonylsulfenyl chloride is slowly added to the mixture, optionally with a few drops of pyridine, and the reaction mixture is heated under reflux for an appropriate time. The desired isocyanate may be recovered from the reaction mixture by cooling, evaporating any residual thionyl chloride, and distillation.

The following are representative examples of the conduct of the process of this invention.

EXAMPLE I

Production of o-Carboxymethylphenylsulfonyl isocyanate

In a flask equipped with a stirrer, reflux condenser, and nitrogen bubbling apparatus were mixed 5 grams (g) (0.023 mole) o-carbomethoxyphenylsulfonamide, 50 milliliters (ml) (0.686 mole) thionyl choride and 2 drops of pyridine. Then, 3 g (0.023 mole) chlorocarbonylsulfenyl chloride was added dropwise. The mixture was heated under reflux (100°–110° C.) under nitrogen, for 12 hours.

The mixture was then cooled to room temperature and the thionyl chloride removed by rotary evaporation. A semi-liquid residue was obtained, which was analyzed by infrared spectroscopy, which indicated the presence of the desired isocyanate. The residue was distilled at 0.1 mm Hg and the product was taken off at 104°–111° C. There was obtained 4.4 g (79% yield) of the desired product, o-carbomethoxyphenylsulfonyl isocyanate. The structure was confirmed by comparison of the infrared spectrum of the product with that of the same compund prepared by reaction of the sulfonamide with phosgene.

EXAMPLE II

Production of 2,5-Dichlorophenylsulfonyl isocyanate

In a flask equipped with a stirrer, reflux condenser, and nitrogen bubbling apparatus, were mixed 5 g (0.022 mole) 2,5-dichlorobenzenesulfonamide and 50 ml (0.686 mole) thionyl chloride. There was then added slowly 2.88 g (0.022 mole) chlorocarbonylsulfenyl chloride, and 2 drops of pyridine was added.

The mixture was heated under reflux for 24 hours, then cooled to room temperature and rotary evaporated. The liquid residue was analyzed by infrared spectroscopy, which indicated the presence of the desired product. The residue was distilled at 0.1–0.225 mm Hg. The desired product was collected at 105°–124° C. The product was obtained in a yield of 1.9 g (34% of theoretical yield) and the structure was confirmed by comparison of infrared spectra as above.

EXAMPLE III

Production of o-Chlorophenylsulfonyl isocyanate

In a flask equipped with a stirrer, reflux condenser and nitrogen bubbling apparatus, were mixed 5 g (0.03 mole) o-chlorobenzenesulfonamide, 50 ml (0.686 mole) thionyl chloride and 2 drops of pyridine. Then 3.9 g (0.03 mole) chlorocarbonylsulfenyl chloride was slowly added.

The reaction mixture was heated under reflux for 12 hours, then rotary evaporated to produce a liquid residue. The residue was distilled at 0.1–0.5 mm Hg and three fractions were collected: 80°–89° C., 89°–100° C. and 100°–105° C. The three fractions were analyzed by infrared spectroscopy which indicated that all three contained the desired product. The total yield was 3.4 g (52% of theoretical). Structure was confirmed by comparison of infrared spectra as above.

In addition to the compounds whose preparation is demonstrated in the above examples, the process is suitable for the production of substituted phenylsulfonyl or phenoxyphenylsulfonyl isocyanates containing one or more substituents on a phenyl ring. These substituents may include, for instance, halogen, such as chlorine, bromine, fluorine or iodine, haloalkyl (for instance trifluoromethyl), alkyl, alkenyl, alkoxy, alkylthio, hydroxyalkyl, phenoxy, cycloalkyloxy, cyclopropylmethoxy, benzyl, substituted benzyl, nitro, etc. Similarly, substituted naphthylsulfonyl isocyanates may also be prepared, as well as thienyl and furyl isocyanates.

Preferably, the process is carried out utilizing thionyl chloride as the reagent and solvent. However, other solvents may be employed which are compatible with the reactants, products, and reaction conditions, such as chlorobenzene or toluene.

As pointed out, the pyridine catalyst may be added in the mixture of the arylsulfonamide and thionyl chloride, or may alternatively be added subsequently. Alternatively, other tertiary base catalysts may be utilized, such as DABCO or triethylamine.

Preferably the reaction is carried out at the refluxing temperature of the thionyl chloride, which is between about 100°–110° C. However, if additional solvents are utilized, the reaction may be carried out at appropriate temperatures.

The pressure of the reaction is ambient pressure under reflux; however, the pressure may be increased, if desired, to reduce the reaction temperature.

The process of the present invention is generally carried out as described above; however, additional modifications or alternative means may be obvious to those skilled in the art from this disclosure; therefore this invention is limited only by the claims which follow.

What is claimed is:

1. A process for the production of arylsulfonyl isocyanates having the formula

ArSO₂NCO in which Ar represents phenyl, substituted phenyl, phenoxyphenyl, substituted phenoxyphenyl, thienyl, furyl, naphthyl or substituted naphthyl, comprising reacting an arylsulfonylamide having the formula ArSO₂NH₂ with thionyl chloride and chlorocarbonylsulfenyl chloride in the presence of a catalytic amount of a tertiary base.

2. A process according to claim 1 in which the tertiary base is pyridine.

3. A process according to claim 1 in which the reaction is carried out at the reflux temperature of thionyl chloride.

4. A process according to claim 1 in which the arylsulfonylamide is first mixed with the thionyl chloride and the chlorocarbonylsulfenyl chloride is thereafter added in a controlled manner.

5. A process according to claim 1 in which Ar is substituted phenyl.

6. A process according to claim 1 in which the tertiary base is added prior to the addition of chlorocarbonylsulfenyl chloride.

7. A process according to claim 1 in which the tertiary base is added subsequent to the addition of the chlorocarbonylsulfenyl chloride.

* * * * *